(12) United States Patent
McCluskey

(10) Patent No.: US 8,152,776 B2
(45) Date of Patent: Apr. 10, 2012

(54) INFUSION SAFETY STRAP APPARATUS

(76) Inventor: Charles J. McCluskey, St. Petersburg, FL (US)

(*) Notice: Subject to any disclaimer, the term of this patent is extended or adjusted under 35 U.S.C. 154(b) by 0 days.

(21) Appl. No.: 12/592,679

(22) Filed: Dec. 1, 2009

(65) Prior Publication Data
US 2010/0137806 A1 Jun. 3, 2010

Related U.S. Application Data

(60) Provisional application No. 61/200,549, filed on Dec. 2, 2008.

(51) Int. Cl.
*A61M 5/32* (2006.01)
(52) U.S. Cl. ............ 604/179; 604/180; 604/178
(58) Field of Classification Search ............ 604/174, 604/179, 180, 178
See application file for complete search history.

(56) References Cited

U.S. PATENT DOCUMENTS

| 5,406,953 | A | * | 4/1995 | Bui .................... 600/490 |
| 5,449,340 | A | * | 9/1995 | Tollini ................ 602/58 |
| 5,897,519 | A | * | 4/1999 | Shesol et al. ......... 602/79 |

* cited by examiner

*Primary Examiner* — Kevin C Sirmons
*Assistant Examiner* — Brandy C Scott

(57) ABSTRACT

A an arm band or strap is provided adapted to be adjustably and comfortably worn about the wrist or forearm of a patient receiving dialysis treatment. Located on the exterior of the band or strap is a pair of oppositely and axially extending tabs having an underside of hook or loop fastener material complimentary to hook or loop fastener material provided on the band or strap exterior. A pair of infusion tubes are adapted to be removably secured respectively between the tabs and the exterior surface of the strap by the interengaging action of the complimentary hook or loop fastener on the surface of the worn band or strap and the underside of each tab, respectively. The worn strap or arm band and the tabs combine to stabilize the infusion tubes during such treatment all of the while permitting safe use of the patient's hands.

5 Claims, 3 Drawing Sheets

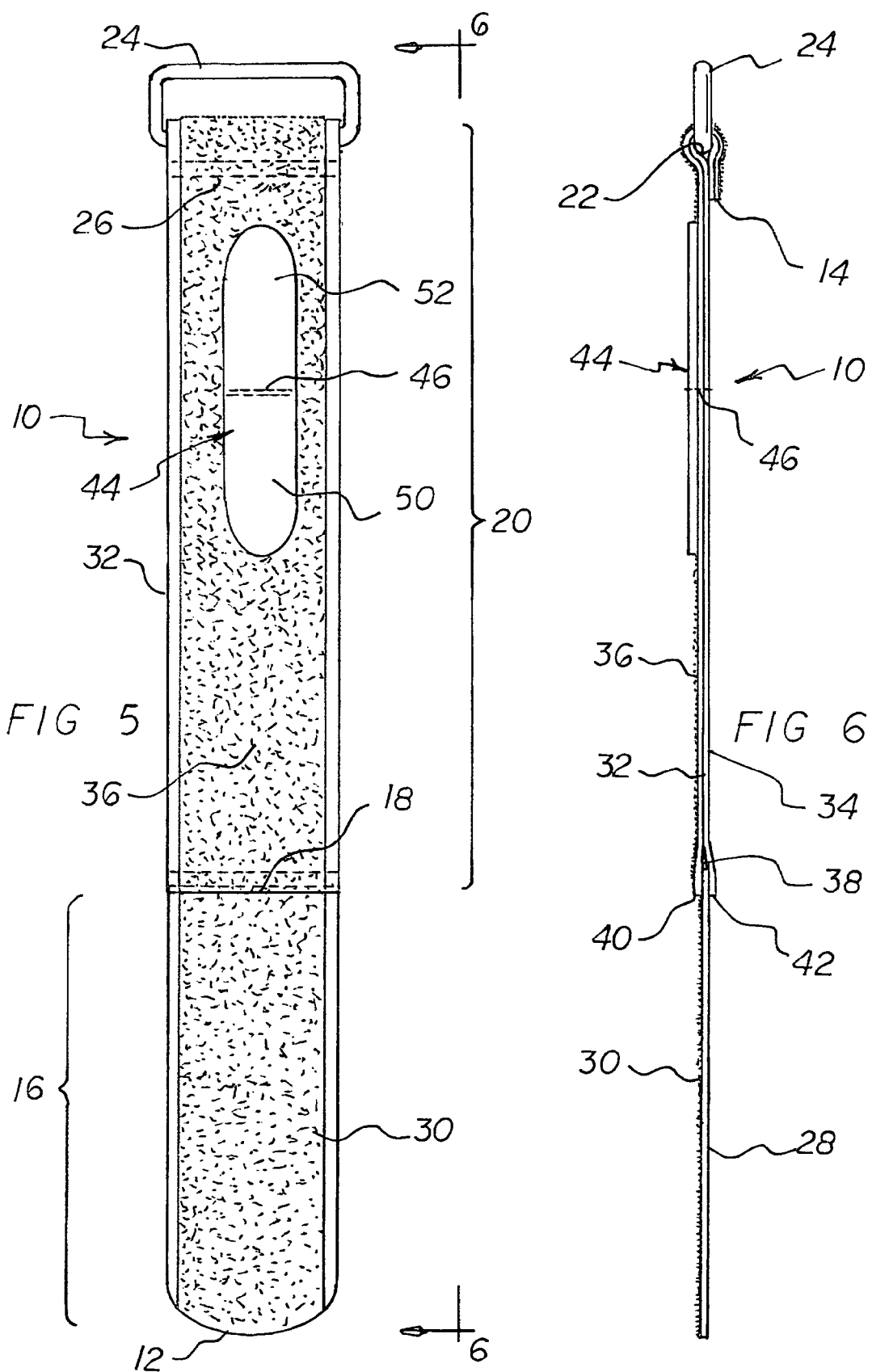

INFUSION SAFETY STRAP APPARATUS

CROSS-REFERENCE TO RELATED APPLICATION

This application claims priority based upon my Provisional Application Ser. No. 61/200,549; filed Dec. 2, 2008.

BACKGROUND OF THE INVENTION

1. Field of the Invention

The present invention relates generally to arm bands (or straps) and more particularly, to a unique arm band or strap construction adapted to safely secure infusion tubing on the arm of a patient undergoing dialysis infusion or a like procedure.

2. Description of the Prior Art

When undergoing dialysis infusion, a pair of tubes typically extending from ports in the patient's arm are employed to provide a circuit for the blood being treated in a dialysis machine located proximal to the patient. One tube is connected to an artery (arterial) and the other tube is connected to a vein (venous). It is difficult for a patient to use their arm when undergoing treatment for fear of snagging one or more of the tubes on a foreign object thereby causing infiltration or dislodgement of the fistula needle during such treatment.

A need exits therefore for an apparatus that can safely secure the arterial and venous infusion tubes in such a manner during dialysis treatments so that infiltrations or dislodgements caused by snagging do not occur. The foregoing desired objects and advantages are provided in accordance with the present invention by providing a unique infusion safety arm band or strap adapted to be worn on a patient's arm generally in the wrist area and which includes manes for removably securing one or more infusion tubes in a fixed spatial relation (stabilized) during the entirety of the dialysis treatment. As will be made apparent from the following description thereof, other advantages of the present invention over the prior art also will be rendered evident.

BRIEF SUMMARY OF THE INVENTION

To achieve the foregoing and other advantages, the present invention, briefly described, provides an arm band or strap having a fastener ring affixed at one end. The opposite portion of the strap at the other opposed end has hook or loop fastener elements (e.g. VELCRO™ fasteners) extending to a transverse seam intermedially located along the strap's longitudinal extent and defining a first section of the strap. Extending from the intermedially located seam to the strap's fastener ring is a second strap section having a layer of complimentary hook or loop fastener elements. Thus when the strap is circumferentially placed about a patient's arm, the first strap section may be inserted through the ring, pulled to a comfortable tension, bent back upon itself, and pressed against the second strap section to removably fasten the sections together by the mating action of complimentary hook or loop fastener elements thereon, respectively. Located upon the second section of the strap is a pair of oppositely and axially extending tabs having hook or loop fastener elements on the underside thereof complimentary to the hook or loop fastener elements on the second section of the strap. A pair of infusion tubes are adapted to be removably secured respectively between the tabs and the surface of the strap's second section by the interengaging action of the complimentary hook or loop fastener elements on the underside of each tab and on the strap's second section, respectively.

The above brief description sets forth rather broadly the more important features of the present invention in order that the detailed description thereof that follows may be better understood, and in order that the present contributions to the art may be better appreciated. There are, of course, additional features of the invention that will be described hereinafter and which will be for the subject matter of the claims appended hereto.

In this respect, before explaining a preferred embodiment of the invention in detail, it is understood that the invention is not limited in its application to the details of the construction and to the arrangements of the components set forth in the following description or illustrated in the drawings. The invention is capable of other embodiments and of being practiced and carried out in various ways. Also, it is to be understood, that the phraseology and terminology employed herein are for the purpose of description and should not be regarded as limiting.

As such, those skilled in the art will appreciate that the conception, upon which disclosure is based, may readily be utilized as a basis for designing other structures, methods, and systems for carrying out the several purposes of the present invention. It is important, therefore, that the claims be regarded as including such equivalent constructions insofar as they do not depart from the spirit and scope of the present invention.

It is therefore an object of the present invention to provide a new and improved infusion safety arm band or strap apparatus which has all of the advantages of the prior art and none of the disadvantages.

It is another object of the present invention to provide a new and improved infusion safety arm band or strap apparatus which may be easily and efficiently manufactured and marketed.

It is a further object of the present invention to provide a new and improved infusion safety arm band or strap apparatus which is of durable and reliable construction.

An even further object of the present invention is to provide a new and improved interchangeable infusion safety arm band or strap apparatus which is susceptible of a low cost of manufacture with regard to both materials and labor, and which accordingly is then susceptible of low prices of sale to the consuming public, thereby making such shovel apparatus available to the buying public.

Still yet a further object of the present invention is to provide a new and improved infusion safety arm band or strap apparatus adapted to be easily removably, fastened about the arm or wrist of a patient undergoing dialysis treatment.

Yet still a further object of the present invention is to provide a new and improved infusion safety arm band or strap apparatus adapted to be easily removably fastened about the arm or wrist of a patient undergoing dialysis treatment, and which further includes separate openable and closeable securement manes for a pair of infusion tubes, respectively.

Still yet a further object of the present invention is to provide a new and improved infusion safety arm band or strap apparatus adapted to be easily removably fastened about the arm or wrist of a patient undergoing dialysis treatment, and which further includes separate openable and closeable securement manes for a pair of infusion tubes, respectively, in the form of a pair of oppositely extending lift tabs hingedly affixed on the outer facing surface of the arm or strap when the latter is worn on a patient and whereupon the tabs are openable and closeable by the interengaing action of complimentary hook or loop fastener on the bottom surface of each tab and the opposing surface of the arm band or strap.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

The invention will be better understood and the above objects as well as objects other than those set forth above will become more apparent after a study of the following detailed description thereof. Such description makes reference to the annexed drawing wherein:

FIG. 5 is a plan view of the arm band or strap of the invention in an unfolded (unused) condition.

FIG. 6 is a side view in elevation of the arm or strap of FIG. 5 taken along line 6-6 of FIG. 5.

DESCRIPTION OF THE PREFERRED EMBODIMENT

Figure 1:
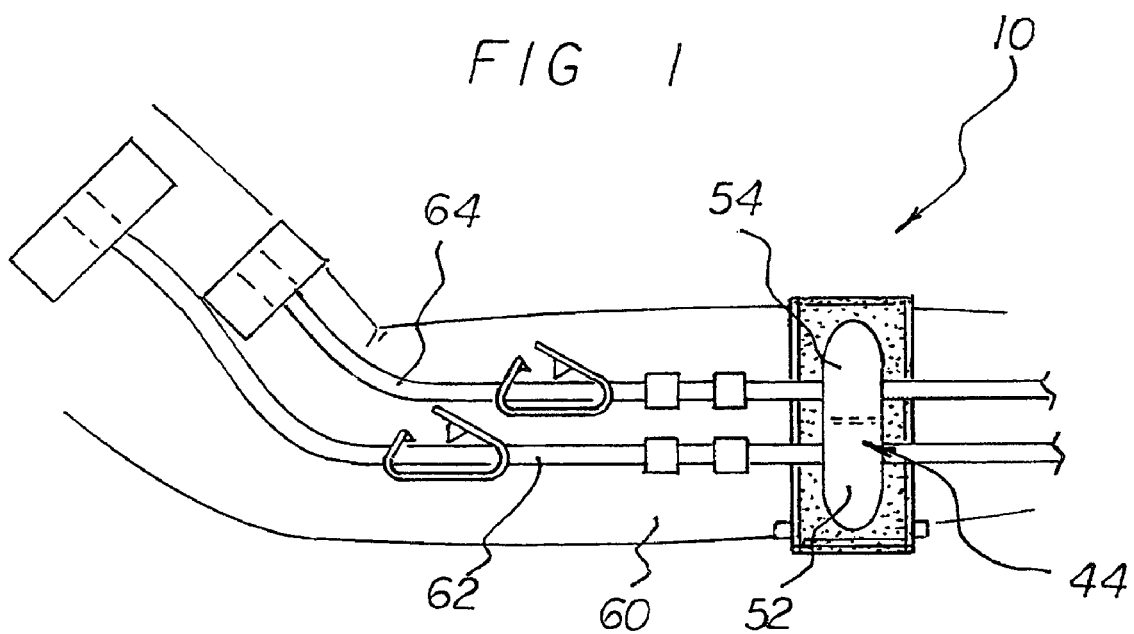
FIG. 1 is a view schematically showing the arm band or strap of the present invention fastened about the arm of a patient undergoing dialysis treatment.
Figure 2:
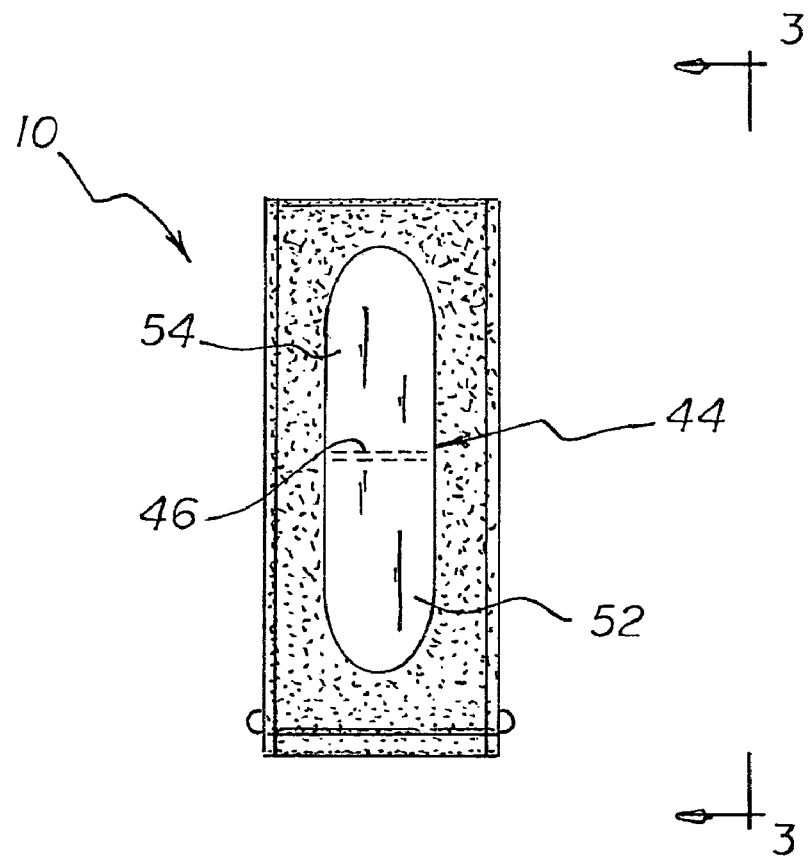
FIG. 2 is an enlarged view of the arm band or strap of the present invention of FIG. 1 showing the securement lift tabs thereon.

With reference to the drawings, a new and improved infusion safety band or strap apparatus embodying the principles and concepts of the present invention will be described.

Turning initially to FIGS. 5-6, there is shown a preferred embodiment of the band or strap apparatus of the present invention generally represented by reference numeral 10 shown for illustration purposes in a flat or unfolded condition. Band or strap apparatus 10 has a first end 12 and an opposed second end 14. A first longitudinal section 16 extends from first end 12 to an intermedially situated transverse seam 18. A second longitudinal section 20 extends form seam 18 to second end 14. Second end 14 is turned back against itself to form a loop 22 for capturing a substantially rectangular or oblong shaped strap fastener ring 24, substantially as depicted. A transverse seam 26 as by sewing maintains loop in place and secures the ring 24 at second end 14.

In accordance with the invention, band or strap 10 is fabricated from a tough, durable, flexible woven or non-woven fabric material. NYLON, for example, is quite suitable and mostly preferred. First longitudinal section 16 comprises a first ply or layer 28, substantially coextensively covered by hook or loop fastener elements 30. Such material is well known and commercially available under the VELCRO trademark. Second longitudinal section 20 preferably is comprised of a pair of second and third plies or layers 32, 34 coextensively superimposed one on top of the other substantially as shown (FIG. 6). Top or second ply or layer 32 comprises hook or loop fastener elements 36 complimentary to the hook or loop fastener elements 30 of first ply or layer 28. Bottom or third ply or layer 34 comprises a substantially smooth cushioning layer adapted to comfortably engage the wrist or forearm of a patient. Third ply or layer 34 suitably may be coextensively attached or otherwise joined to the second or top layer 32 as by sewing, heat bonding, or any other known technique.

Substantially as shown in FIGS. 5 and 6, first longitudinal section 16 preferably is joined to second longitudinal section 20 as by sewing or the like along first transverse seam 18 with the edge 38 of the first longitudinal section 16 being received within and between the confronting edges 40, 42 of second and third plies or layers 32, 34. In accordance with the present invention, an infusion tube securement tab 44 in the form of length of rectangular or oblong shaped flexible material is fastened as by sewing or the like to at least second ply or layer 32 by means of a third transverse seam 46 substantially as depicted. Thus Tab 44 is positioned on second ply or layer 32 with its longitudinal axis generally aligned with the longitudinal axis of band or strap apparatus 10 and furthermore with the tab 44 being situated proximal to fastener ring 24 (FIG. 5).

Figure 4:
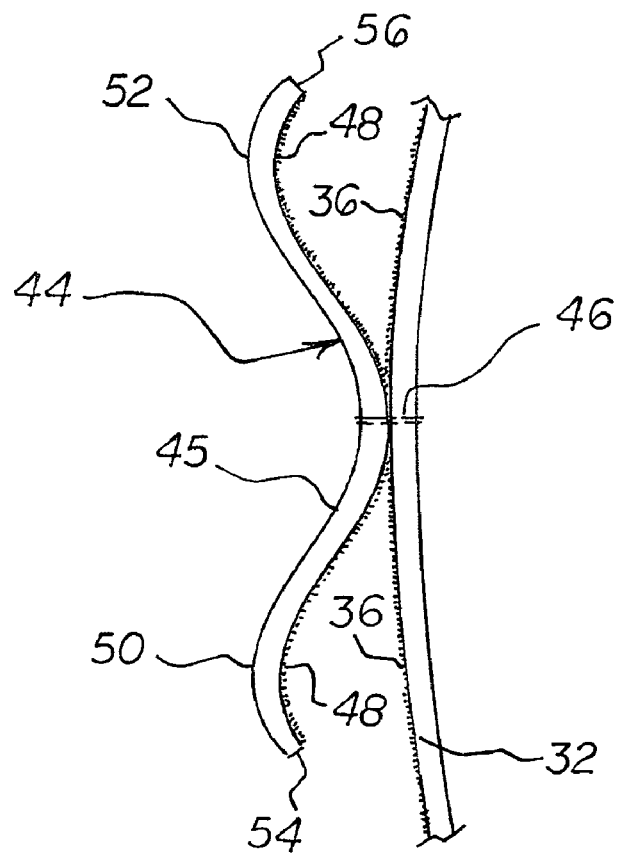
FIG. 4 is a enlarged view of a portion of the arm band or strap shown in FIG. 3.

As best seen in FIG. 4, third seam 46 which extends transversely of tab 44 substantially centrally thereof (FIG. 5), defines a pair of oppositely extending first and second tab portions 50, 52 each having a free edge 54, 56, respectively. Additionally, third seam 44 functions as a hinge facilitating lifting of each tab toward and away from the confronting surface of second or top layer 32. Moreover, it will be appreciated that tab 44 also is fabricated of hook or loop fastener material, substantially smooth on the top surface 45 thereof, with hook or loop fastener elements 48 on the bottom surface thereof, and that the hook or loop fastener elements 48 of tab 44 are complimentary to the hook or loop fastener elements 36 on the confronting surface of second top ply or layer 32. Because tab 44 is seamed in the middle so-to-speak (FIG. 4), the oppositely extending first and second tab portions 50, 52 individually may conveniently be unfastened from second top ply or layer 32 (FIG. 6) by pulling away therefrom, or conveniently refastened thereto to secure a corresponding infusion tube thereunder as will be more fully described below.

Figure 3:
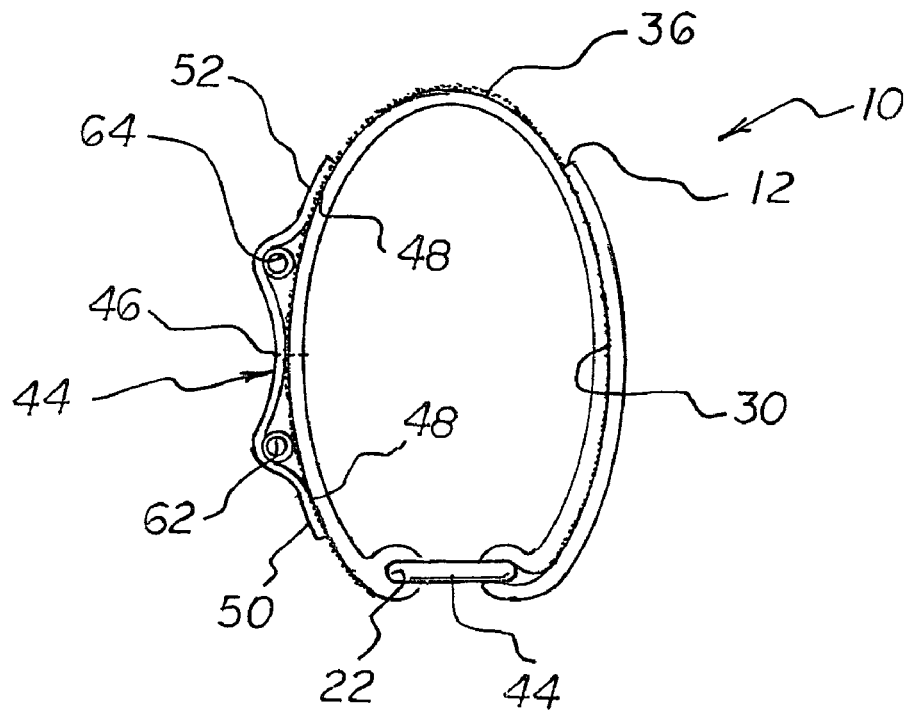
FIG. 3 is plan view of the strap or band of FIG. 2 taken along line 3-3 of FIG. 2 and showing how one end of the strap is adjustably affixed to the strap in the worn position with respect to a patient's arm or wrist.

The infusion safety arm band or strap 10 is schematically depicted in FIG. 1 in use on a patient's arm 60 to stabilize a pair of infusion tubes 62, 64 during dialysis treatment. In use, the band or strap apparatus 10 easily may be comfortably adjustably circumferentially fitted about the forearm or wrist 60 of a patient by merely inserting the first end 12 through ring 24, folding it back and pressing the first section 16 against the second top layer 32 until the complimentary hook or loop fastener elements 30, 36 suitably matingly engage (FIG. 3). Then the tab portions 50, 52 are pulled or lifted away from the top layer 32 of the strap (FIG. 4) and one or more infusion tubes 62, 64 may be placed underneath tabs portions 50, 52 and secured in place by pressing the tab sections against the second top layer until the hook or loop fastening elements 48 suitably matingly engage with complimentary hook or loop fastening elements 36 (FIGS. 1 and 3). To remove the infusion tubes 62, 64 and arm band or strap apparatus 10 following completion of a dialysis procedure, the foregoing process merely is reversed.

The infusion safety band or strap of the present invention may be fabricated in a variety of sizes to fit adults, children or even infants. To merely illustrate without limiting the present invention in any way, an "adult size" version can be fabricated having a longitudinal dimension of about 13 inches including the fastener ring, a transverse dimension of about 1 and ½ inches, with the lift tabs 50, 52 being about 3 inches in length, with the lift tab seam 46 being located about 3 and ¼ inches from the distal end of the fastener ring 24, with seam 18 being located about 4 and ½ inches from end 12 (see FIG. 5).

The infusion safety band or strap 10 of the present invention may be commercially distributed under the trademark HEMASTRAP.

The components of the infusion safety band or strap apparatus of the present invention can be made from inexpensive and durable metal, plastic or cloth materials.

As to the manner of usage and operation of the instant invention, the same is apparent from the above disclosure, and accordingly, no further discussion relative to the manner of usage and operation need be provided.

It is apparent from the above that the present invention accomplishes all of the objects set forth by providing a new and improved infusion band or strap apparatus that is low in cost, relatively simple in design and operation, and which may advantageously be used to provide a safe and effective way to stabilize infusion tubing during dialysis procedures or the like and to facilitate use of a patient's hands during such treatment substantially obviating any concerns that such use will cause snagging of the tubing on foreign objects leading to undesired infiltration or dislodgement of the fistula needle.

Thus, while the present invention has been shown in the drawings and fully described above with particularity and detail in connection with what is presently deemed to be the most practical and preferred embodiment(s) of the invention, it will be apparent to those of ordinary skill in the art that many modifications thereof may be made without departing from the principles and concepts set forth herein, including, but not limited to, variations in size, materials, shape, form, function and manner of operation, assembly and use.\ Hence, the proper scope of the present invention should be determined only by the broadest interpretation of the appended claims so as to encompass all such modifications as well as all relationships equivalent to those illustrated in the drawings and described in the specification.

Finally, it will be appreciated that the purpose of the annexed Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

What is claimed as being new and desired to be protected by Letters Patent of the United States is as follows:

1. Arm band apparatus for securing one or more infusion tubes during medical treatment of a patient, comprising:

an arm band, said arm band having an adjustable fastener for circumferentially fitting said arm band about said arm of said patient, said arm band having first and second opposed surfaces, said first surface facing exteriorly and said second surface engaging said patient's arm when said strap is adjustably circumferentially fitted on said arm of said patient, and means mounted said first surface for engaging at least one infusion tube in a fixed manner relative to said arm band first surface when said arm is fitted on a patient's arm as aforesaid, wherein said means mounted on said first surface comprises at least one lift tab hingedly attached to said first surface, wherein said first surface has a longitudinal extent, and said lift tab has a length dimension extending commonly along the longitudinal extent of said first surface, and wherein said lift tab is attached to said first exteriorly facing surface of said arm band along a transverse seam located intermedially of said length dimension to define first and second lift tab portions thereof extending oppositely with respect to each other, said first and second lift tab portions defining a pair of distal free ends co-axially oriented with respect to each on either side of said transverse seam respectively, such that said distal free ends of said first and second lift tab portions extend co-axially with respect to each other on opposite sides of said transverse seam along said length dimension of said at least one lift tab, and wherein said first and second lift tab portions each has a top surface and a bottom surface respectively with respect to said arm band exteriorly facing surface, said bottom surface of said first and second lift tab portions each has fastener elements thereon respectively, and said exteriorly facing surface of said arm band has fastener elements thereon complimentary to said fastener elements on said bottom surface of said first and second lift tab portions whereby at least a pair of separate infusion tubes may be supported relative to said exteriorly facing surface of said arm band on opposite sides of said transverse seam respectively when said first and second lift tab portions are fastened to said exteriorly facing surface of said arm band by engagement of the complimentary fastener elements on said bottom surface of said first and second lift tab portions and said exteriorly facing surface of said arm band.

2. The apparatus of claim 1 wherein said fastener elements on said first surface includes hook or loop fastener elements thereon, and said fastener elements on said lift tab portions comprise hook or loop fastener elements thereon complimentary to said hook or loop fastener elements on said first surface.

3. The apparatus of claim 2 wherein said arm band includes a first end and a second opposed end, and said adjustable fastener includes a fastener ring affixed to said arm band second opposed end.

4. The apparatus of claim 3 wherein said arm band first surface includes a portion proximal to said first end of said arm band, and said portion includes hook or loop fastener elements thereon, said hook or loop fastener elements on said portion proximal to said first end being complimentary to the said hook or loop fastener elements on said first surface such that when said first end of said arm band is inserted through said fastener ring and folded back upon itself, said hook or loop fastener elements on said portion proximal to said first end are adapted to mutually engage said complimentary hook or loop fastener elements on said first surface of said arm band.

5. The apparatus of claim 3 wherein said at least one lift tab hingedly attached to said first surface is located proximal to said fastener ring and distally with respect to said arm band first end.

* * * * *